(12) United States Patent
Van Roemburg

(10) Patent No.: US 7,913,933 B2
(45) Date of Patent: Mar. 29, 2011

(54) ESSENTIAL OIL ATOMISER

(75) Inventor: John Van Roemburg, Brighton (AU)

(73) Assignee: Air Aroma Research Pty. Limited, Sandringham, Victoria (AU)

( * ) Notice: Subject to any disclaimer, the term of this patent is extended or adjusted under 35 U.S.C. 154(b) by 190 days.

(21) Appl. No.: 11/568,550

(22) PCT Filed: May 4, 2005

(86) PCT No.: PCT/AU2005/000639
§ 371 (c)(1),
(2), (4) Date: Nov. 1, 2006

(87) PCT Pub. No.: WO2005/105163
PCT Pub. Date: Nov. 10, 2005

(65) Prior Publication Data
US 2007/0163577 A1    Jul. 19, 2007

(30) Foreign Application Priority Data
May 4, 2004 (AU) .................................. 2004902366

(51) Int. Cl.
*A61M 11/06* (2006.01)
(52) U.S. Cl. ......... 239/338; 239/339; 239/342; 239/427
(58) Field of Classification Search .......... 239/337–340, 239/34, 342, 427; 422/123, 124
See application file for complete search history.

(56) References Cited

U.S. PATENT DOCUMENTS

| | | | | |
|---|---|---|---|---|
| 2,302,185 A * | 11/1942 | Campbell, Jr. | ................ | 239/707 |
| 2,302,289 A * | 11/1942 | Bramston-Cook | ............... | 239/3 |
| 3,701,480 A * | 10/1972 | Kuhner et al. | ................ | 239/420 |
| 4,657,007 A * | 4/1987 | Carlin et al. | ............. | 128/200.18 |
| 4,938,416 A | 7/1990 | Bertrand et al. | | |
| 5,012,961 A * | 5/1991 | Madsen et al. | ................ | 222/643 |
| 5,029,729 A * | 7/1991 | Madsen et al. | ..................... | 222/1 |
| 5,549,247 A | 8/1996 | Rossman et al. | | |
| 5,635,132 A | 6/1997 | Blanc | | |
| 6,012,647 A * | 1/2000 | Ruta et al. | .................. | 239/132.1 |
| 6,189,810 B1* | 2/2001 | Nerushai et al. | .............. | 239/306 |
| 6,238,646 B1 | 5/2001 | Zembrodt | | |
| 6,405,944 B1* | 6/2002 | Benalikhoudja | .............. | 239/338 |
| 6,645,436 B2 | 11/2003 | Davis | | |
| 6,802,460 B2* | 10/2004 | Hess et al. | ..................... | 239/306 |
| 2002/0068023 A1* | 6/2002 | Davis | ........................... | 422/124 |
| 2003/0192959 A1* | 10/2003 | Hess et al. | ...................... | 239/69 |
| 2005/0077383 A1* | 4/2005 | Sevy | ............................. | 239/290 |
| 2006/0011739 A1* | 1/2006 | Jaworski | .................... | 239/102.2 |

FOREIGN PATENT DOCUMENTS
WO      WO 03/008001 A1     1/2003
* cited by examiner

*Primary Examiner* — Dinh Q Nguyen
(74) *Attorney, Agent, or Firm* — Edwin D. Schindler

(57) ABSTRACT

An oil atomizer apparatus for essential and fragrant oils includes at least one atomizer that engages with a container of essential and fragrant oils, and a body with a generally hollow interior and having a mixer housing associated with one surface of the body. An oil feeder tube extends from the mixer housing and through a surface of the body to the container of essential and fragrant oils. The mixer housing includes a compressed air inlet of a first diameter which is larger than a second diameter of the inlet, which passes to a diffusion chamber in the mixer housing having a passage to the body of the container. The application of compressed air to the inlet of the mixer housing causes the essential and fragrant oils to be dispersed to air in a fine droplet form through at least one aperture in the body.

4 Claims, 1 Drawing Sheet

ESSENTIAL OIL ATOMISER

AREA OF THE INVENTION

Figures 1, 2:
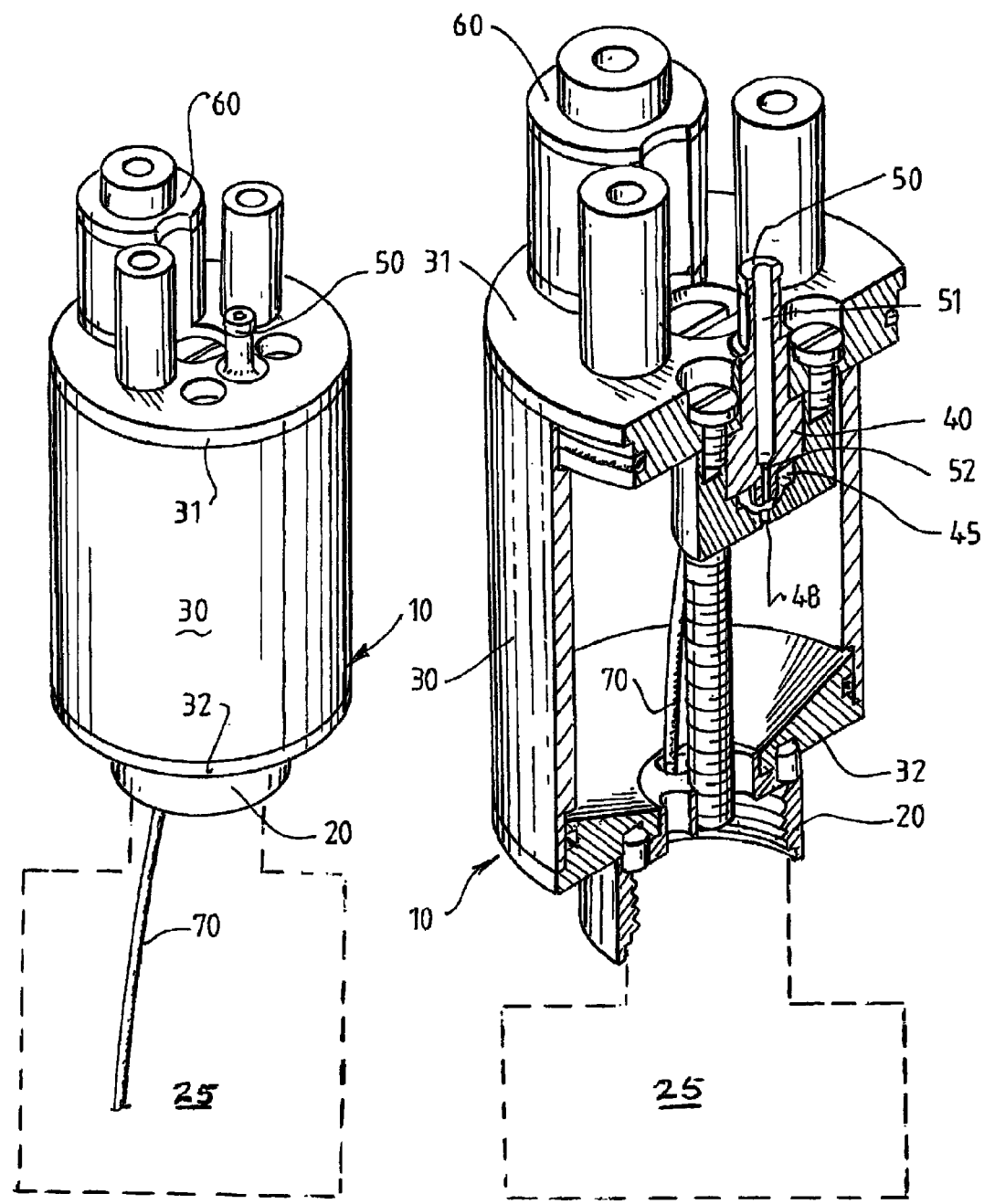

This invention relates to the area of equipment for use with oils both fragrant and essential and in particular to an atomizer which is able to be used to spray these oils into the air.

BACKGROUND TO THE INVENTION

While the invention relates to an atomizer for use with both essential and fragrant oils it will be discussed here for convenience's sake in terms of its application to essential oil dispersion.

Essential oil dispersion in air has become a popular method of eliminating unwanted odours in the ambient environment and opposing air borne microbes or bacteria, viruses and moulds among other things. Among the other attributes of essential oil dissemination in the atmosphere is that it is believed to promote a healthy pleasant and positive environment.

It is believed that each essential oil has its own unique properties that are therapeutic in the human body in a holistic way and that they provide benefit both physically by inhaling droplets and psychologically via the sense of smell. The theory is that the aroma of an essential oil can induce a number of intricate responses including sensory stimulation, relaxation and a sense of well being.

Many essential oil dispersion means involve heating the oil until it vaporises and diffuses through a room. A problem with this approach is the fact that open flames can be a fire hazard and also it is considered by many that cold air diffusion is the only method which preserves the full integrity of the properties of the essential oil.

OUTLINE OF THE INVENTION

It is an object of this invention to provide a means whereby essential and fragrant oils are able to be disseminated in droplet form without the application of heat to the oil.

The invention is an oil atomiser system for essential and fragrant oils having at least one atomiser which is adapted to engage with a container of said oil, said atomiser having a body with a generally hollow interior and having a mixer housing associated with one surface thereof from which housing an oil feeder tube extends through a surface of the body to the container, the mixer housing having also a compressed air inlet with a first diameter which is larger than a second diameter of the inlet which passes to a diffusion chamber in the mixer housing having a passage to the body of the container such that application of compressed air to the inlet causes the oil to be dispersed to air in fine droplet form through at least one aperture in the body.

It is preferred that the mixer housing is located inside the body and is integral with an upper surface thereof.

It is further preferred that the body have a vertical height which is such that a single plume of oil droplets is formed as an air/oil mix exits the mixer housing to the atomizer body.

It is preferred that the compressed air be provided by an air compressor associated with the system.

It is further preferred that the application of the compressed air cause essential oil to be drawn into the mixer housing and passed through a diffusion chamber to leave the system as an essential oil/air micromist mixture.

It is preferred also that a plurality of atomisers may be provided in a given housing. It is further preferred that a plurality of atomisers in a housing may be programmed to function at different times of day either by timing means or programmable means.

In order that the invention may be more readily understood we will describe by way of non limiting example a specific embodiment of the invention.

BRIEF DESCRIPTION OF THE DRAWING FIGURES

FIG. 1 Shows a perspective view of the atomizer of the invention;

FIG. 2 Shows a sectional view through the atomizer;

DESCRIPTION OF AN EMBODIMENT OF THE INVENTION

Although the concept of the invention can applied to many different styles of essential or fragrant oil atomizer a particular embodiment of the atomizer system will be described here in terms of its application to essential oil dispersion. It is of course to be understood that variations in physical design, manufacturing materials and size can still lie within the scope of the invention.

In this particular embodiment of the invention, an essential oil atomizer 10 is provided, which is provided with engagement means, in this case a screw threaded portion 20 of body portion 30, to engage with the neck of an open bottle of essential oil 25, which is shown in phantom.

Above this engagement means the atomizer system is provided with a generally cylindrical housing or body 30 for its component parts which may be of stainless steel or any other preferred material. The interior of this housing holds a mixer housing 40 having a diffusion chamber 45.

The arrangement is such that an external compressed air supply passes through an compressed air inlet 50 into the mixer housing 40 thereby causing essential oil to be drawn through a tube 70 passing from the essential oil bottle and terminating in the mixer housing 40.

The compressed air inlet 50 has an initially wider bore 51, the air then passes through a smaller bore 52 to the diffusion chamber 45 where the oil is broken down into small droplets which pass through a narrow aperture 48 into the interior of the atomizer body 30.

The resultant mixture then passes through at least one oil mist outlet 60 in an upper surface of the system housing 30 to be dispersed as an essential oil/air mixture as a micromist.

This ability to successfully break an essential oil up into a fine droplet distribution which is capable of remaining airborne is achieved without the use of heat to either vaporise the oil or vaporise water droplets carrying the oil.

The effect is achieved by the compressed air supply passing from the initial air supply jet into a finer tube at a terminal end of the first jet or tube. By this means the resulting jet enhances the essential oil atomisation into small droplets capable of being effectively dispersed to the environmental air.

In this embodiment of the invention the system housing includes a top cap 31 and a bottom cap 32 which engage with its central body 30 in sealing engagement with the provision of appropriate O rings. The system housing is maintained in its assembled configuration by screw means.

While this is the arrangement preferred in this embodiment of the invention it is envisaged that any interconnection means of the component parts could be used and that the actual system housing components could vary both in their arrangement and in their appearance. The fundamental means whereby the essential oil was able to be atomised and dispersed would of course be common to all models of the atomizer.

While we have described herein one specific embodiment of the invention it is envisaged that other embodiments of the invention will exhibit any number of and any combination of the features of those previously described and it is to be understood that variations and modifications in this can be made without departing from the spirit and scope of the invention.

The invention claimed is:

1. An atomizer for essential and fragrant oils, comprising:

a body engagable with a container of essential and fragrant oils, said body having a substantially hollow interior and a mixer housing integral with an upper surface thereof, said mixer housing being a closed structure except for a compressed air inlet, a tubular aperture leading from said mixer housing, the compressed air inlet having a first diameter which is larger than a second diameter of the tubular aperture, and an oil feeder tube;

said oil feeder tube extending from said mixer housing through said body to the container of essential and fragrant oils; and, a diffusion chamber defined by the substantially hollow interior of said body, the compressed air inlet of said mixer housing providing downwardly directed compressed air, so that droplets of oil are formed in said mixer housing before passing down through the tubular aperture to said diffusion chamber for forming finer droplets which then pass from said body through an aperture therein.

2. The atomizer for essential and fragrant oils according to claim 1, wherein said mixer housing is located inside said body and is integral with the upper surface of said body.

3. The atomizer for essential and fragrant oils according to claim 1, wherein said body has a vertical height by which a single plume of finer oil droplets is formed as an oil/air micromist mixture exits said mixer housing of said body.

4. The atomizer for essential and fragrant oils according to claim 1, wherein said body includes a threaded portion for engaging a container of essential and fragrant oils.

* * * * *